US012577203B2

(12) United States Patent
Klopsch et al.

(10) Patent No.: US 12,577,203 B2
(45) Date of Patent: Mar. 17, 2026

(54) SOLUTION OF TEMPO-DERIVATIVES FOR USE AS ELECTROLYTE IN REDOX-FLOW CELLS

(71) Applicant: BASF SE, Ludwigshafen am Rhein (DE)

(72) Inventors: Rainer Klopsch, Ludwigshafen am Rhein (DE); Peter Oechsle, Ludwigshafen am Rhein (DE); Harald Winsel, Ludwigshafen am Rhein (DE); Alexander Michael Haydl, Ludwigshafen am Rhein (DE); Joaquim Henrique Teles, Ludwigshafen am Rhein (DE); Johann-Peter Melder, Ludwigshafen am Rhein (DE); Jan-Dirk Arndt, Ludwigshafen am Rhein (DE); Olaf Kriha, Ludwigshafen am Rhein (DE); Alexandre Guthertz, Ludwigshafen am Rhein (DE)

(73) Assignee: BASF SE, Ludwigshafen Am Rhein (DE)

( * ) Notice: Subject to any disclaimer, the term of this patent is extended or adjusted under 35 U.S.C. 154(b) by 706 days.

(21) Appl. No.: 17/915,116

(22) PCT Filed: Mar. 22, 2021

(86) PCT No.: PCT/EP2021/057182
§ 371 (c)(1),
(2) Date: Sep. 28, 2022

(87) PCT Pub. No.: WO2021/197877
PCT Pub. Date: Oct. 7, 2021

(65) Prior Publication Data

US 2023/0150938 A1 May 18, 2023

(30) Foreign Application Priority Data

Apr. 1, 2020 (EP) .................................... 20167458

(51) Int. Cl.

| | |
|---|---|
| ***C07D 211/58*** | (2006.01) |
| ***H01M 8/08*** | (2016.01) |
| ***H01M 8/18*** | (2006.01) |

(52) U.S. Cl.
CPC ............ *C07D 211/58* (2013.01); *H01M 8/08* (2013.01); *H01M 8/188* (2013.01); *H01M 2300/0005* (2013.01)

(58) Field of Classification Search
CPC ...... C07D 211/58; C07D 211/94; H01M 8/08; H01M 8/188; H01M 2300/0005; Y02E 60/50; Y02P 70/50
See application file for complete search history.

(56) References Cited

U.S. PATENT DOCUMENTS

2018/0241065 A1 8/2018 Schubert et al.

FOREIGN PATENT DOCUMENTS

| | | | |
|---|---|---|---|
| DE | 102015010083 A1 | 2/2017 | |
| DE | 102016009904 A1 | 2/2018 | |
| WO | 2014/026728 A1 | 2/2014 | |
| WO | WO-2018028830 A1 * | 2/2018 | ........... C07D 211/94 |

OTHER PUBLICATIONS

Schubert (WO2018028830 (A1) and using Machine Translation as English version) (Year: 2018).*
International Search Report and Written Opinion received for PCT Patent Application No. PCT/EP2021/057182, mailed on Jun. 30, 2022, 12 pages.
European Search Report for EP Patent Application No. 20167458.7, Issued on Oct. 14, 2020, 4 pages.
Hu et al., "Improved radical stability of viologen anolytes in aqueous organic redox flow batteries," Chemical Communications, vol. 54, No. 50, Jun. 19, 2018, pp. 6871-6874.
International Preliminary Report on Patentability received for PCT Patent Application No. PCT/EP2021/057182, mailed on Oct. 13, 2022, 8 pages.
Janoschka et al., "An Aqueous Redox-Flow Battery with High Capacity and Power: The TEMPTMA/MV System," Angewandte Chemie, vol. 55, Issue 46, Nov. 7, 2016, pp. 14427-14430.

* cited by examiner

*Primary Examiner* — Milton I Cano
*Assistant Examiner* — Joshua P McClure
(74) *Attorney, Agent, or Firm* — Faegre Drinker Biddle & Reath LLP

(57) ABSTRACT

The present invention relates to a solution comprising water and different 2,2,6,6-tetramethyl-piperidinyl-oxyl (TEMPO)-derivatives, a process for the production of this solution, a process for making a redox-flow cell comprising the solution as electrolyte, the redox-flow cell comprising the solution as an electrolyte in one chamber of the cell and the use of the redox-flow cell for storing electrical energy.

12 Claims, 2 Drawing Sheets

SOLUTION OF TEMPO-DERIVATIVES FOR USE AS ELECTROLYTE IN REDOX-FLOW CELLS

CROSS-REFERENCE TO RELATED APPLICATIONS

This application is a national stage application (under 35 U.S.C. § 371) of PCT/EP2021/057182, filed Mar. 22, 2021, which claims benefit of European Application No. 20167458.7 filed Apr. 1, 2020, both of which are incorporated herein by reference in their entirety.

The present invention relates to a solution comprising water and different 2,2,6,6-tetramethylpiperidinyl-oxyl (TEMPO)-derivates, a process for the production of this solution, a process for making a redox-flow cell comprising the solution as electrolyte, the redox-flow cell comprising the solution as an electrolyte in one chamber of the cell and the use of the redox-flow cell for storing electrical energy.

There is a huge demand for storing electrical energy for different kind of applications. It was found that redox-flow cells with new organic compounds as redox couple comprising 2,2,6,6-tetramethylpiperidinyl-oxyl (TEMPO)-derivates with redox active potential separated from each other by using a membrane which selects the molecules by size might be an easy and inexpensive way to provide a long-living redox-flow cell which will not have a negative impact on the environment as it is described in WO 2014/26728.

WO2018/028830 describes a process of the production of 4-ammonium-2,2,6,6-tetraalkylpiperidinyl salts as typical TEMPO-derivates which are such redox active compounds that are normally used in the cathode chamber of a redox-flow cell. It is disclosed that for the production of these compounds 3 different production ways are possible. Starting products are always solutions of either 4-oxo-alkylpiperidine, the corresponding imine or 4-amino-alkylpiperidine dissolved in different kinds of organic aprotic solvents like alcohols, ethers, nitriles, halogenated hydrocarbons, aromatic hydrocarbons, aliphatic hydrocarbons or mixtures of them. In two production ways described in WO 2018/028830 the intermediate compounds are solids which have to be separated from the solvent before using them in the next step. With these described production processes, a very pure final compound is obtained but there are many intermediate stages where solids have to be handled, different solvents have to be used, or anions have to be exchanged. Furthermore, a production process where only water is used as the solvent is not described. For an industrial scale, the processes described in the state of the art are not appropriate as every filtration step, solvent change or anion exchange step causes great losses in yields and time and generates waste solvent that requires further purification before it can be reused. Furthermore, the use of an aprotic organic solvent in the production process will require at least one solvent change because an aqueous solution is preferred as the electrolyte in the redox-flow cell. The aqueous solution is advantageous as water cannot be easily oxidized or reduced in the redox-flow cell, it is not flammable and therefore safer to handle than an organic solvent, it is not toxic and very inexpensive and easily available.

Therefore, it is an object of the present invention to provide as well an aqueous solution comprising different TEMPO-derivates with chemical redox potential comparable to those isolated pure TEMPO-derivatives described in the state of the art as an easy and inexpensive way of production of this solution where no solid intermediates will have to be separated or handled, no solvent exchange is required and no anion exchange is necessary and which can be used in industrial scale without high efforts and great losses of yield. Another object of the present invention is to provide a redox-flow cell comprising an aqueous solution of TEMPO-derivates that shows similar or identical properties for storing energy as the redox-flow cell comprising an aqueous solution of 2,2,6,6-tetramethyl-1-piperidinyloxy-4-trimethylammonium chloride described in the state of the art.

Figure 1:
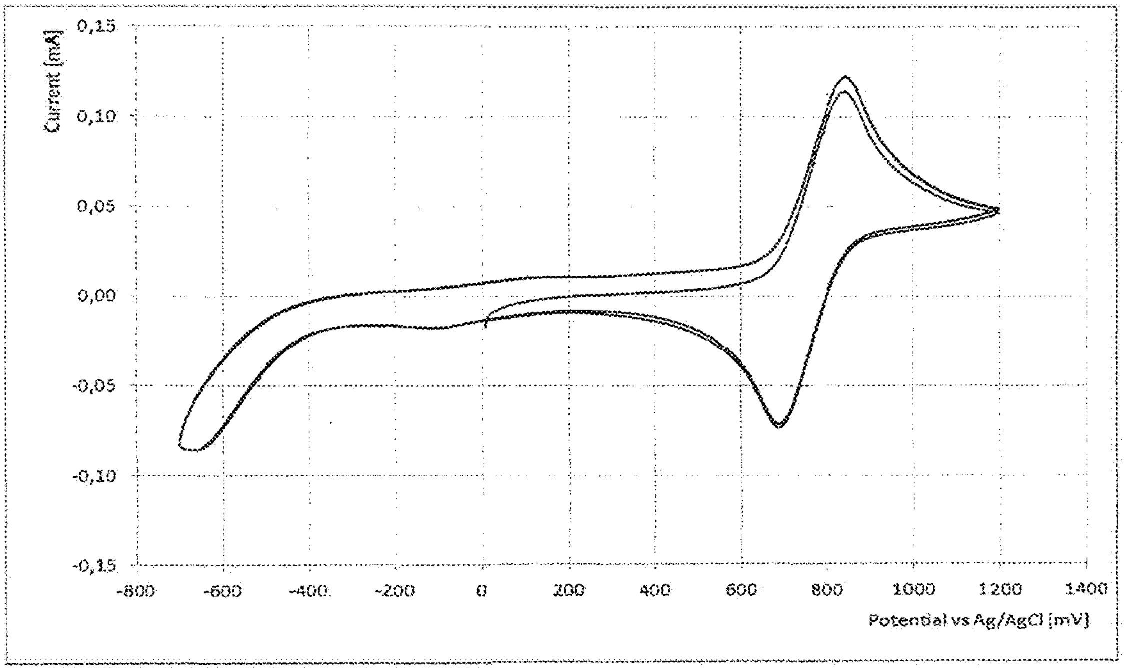
FIG. 1 shows cyclic voltammetry of product of example 3.
Figure 2:
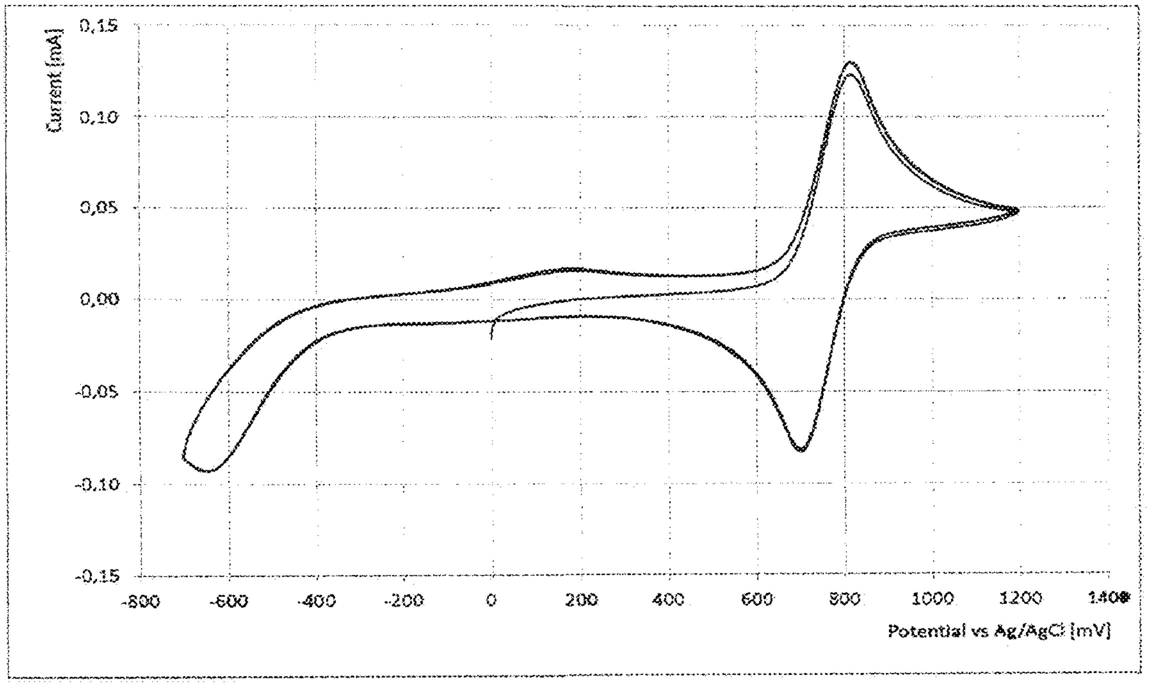
FIG. 2 shows cyclic voltammetry of example 5.

The problem will be solved by a solution comprising a) water, b) 20 to 55 wt.-% according to the total weight amount of the solution of compound 2,2,6,6-tetramethyl-4-(trimethylammonio)-1-piperidinyloxy of formula (I), (I)

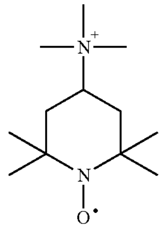

c) 0.1 to 6 wt.-% according to the total weight amount of the solution of an alkali metal cation d) 0.5 to 12.5 wt.-% according to the total weight amount of the solution of compound N,N,N,1,2,2,6,6-octamethyl-4-piperidinammonium-1-oxide of formula (II)

(II)

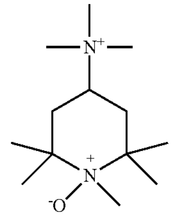

e) 0.1 to 20 wt.-% according to the total weight amount of the solution of compound 2,2,6,6-hexamethyl-4-(dimethylamino)-1-piperidinyloxy-N-oxide of formula (III)

(III)

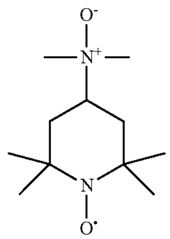

The inventive solution will be advantageous if the alkali metal cation is Na.

The inventive solution will be advantageous if the pH-value is in the range of 2 to 7.

The inventive solution will be advantageous if the sum of the amounts of the compounds of formula (I), (II), (III) plus the amount of alkali metal cations in the solution is in the range of 20 to 50 wt.-% according to the total weight amount of the solution.

The inventive solution will be advantageous if at least 90 mol % of the counterions are chloride ions.

A further embodiment of the invention is a process for the production of the inventive solution comprising the following steps:

i) reacting the compound N,N,2,2,6,6-hexamethyl-4-piperidinamine of formula (IV)

(IV)

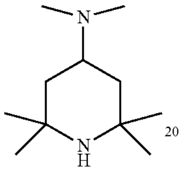

with water and methyl chloride to get an aqueous mixture comprising compound N,N,N,2,2,6,6-heptamethyl-4-piperidinaminium of formula (V), compound N,N,N,1,2,2,6,6-octamethyl-4-piperidinaminium of formula (VI) and non-reacted compound N,N,2,2,6,6-hexamethyl-4-piperidinamine of formula (IV)

(IV)

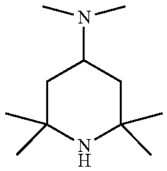

(V)

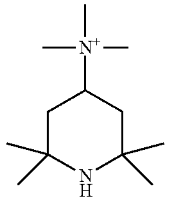

(VI)

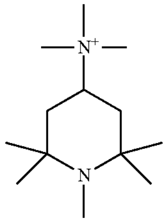

ii) reacting the resulting aqueous mixture of step i) with an aqueous hydrogen peroxide solution in the presence of a catalyst selected from the group of alkali metal carbonate, alkali metal hydrogencarbonate, $CO_2$ and mixtures of those, iii) adding an acid to the mixture obtained in step ii) until the pH-value is in the range of 2 to 7, iv) partially removing water until the concentration of compound of formula (I) is in the range of 20 to 55 wt.-% according to the solution of claim 1.

The inventive process will be advantageous if in step i) of the process the compound of formula (IV) is reacted with methyl chloride and water at a temperature in the range of 0 to 60° C.

The inventive process will be advantageous if in step i) of the process the compound of formula (IV) is reacted with 0.7 to 1.2 equivalents of methyl chloride in the presence of water and the mass ratio between compound of formula (IV) in the feed mixture and water is in the range of 0.1 to 5.

The inventive process will be advantageous if in step ii) of the process the resulting mixture of step i) is reacted with an aqueous hydrogen peroxide solution in the presence of the catalyst at a temperature in the range of 20 to 80° C. wherein the pH-value during the addition of the aqueous hydrogen peroxide solution is maintained between 7 and 10.

The inventive process will be advantageous if in step ii) of the process 1.5 to 5 mol of aqueous hydrogen peroxide having a concentration in the range of 25 to 70 wt.-% are used per mol of compound of formula (IV) in the feed mixture and the reaction is performed in the presence of 0.005 to 0.4 mol of the catalyst per mol of compound of formula (IV) in the feed mixture.

The inventive process will be advantageous if the addition of the acid in step iii) starts when the concentration of hydrogen peroxide in the mixture of step ii) has decreased to less than 0.5 wt. %.

The inventive process will be advantageous if the acid in step iii) is hydrogen chloride.

A further embodiment of the invention is a process for making a redox-flow cell wherein the inventive solution is used as electrolyte in one of the two chambers of the cell.

The inventive process for making a redox-flow cell will be advantageous if the process comprises the following steps:

a) providing two chambers for catholyte and anolyte solutions, each connected to at least one storage tank for catholyte and anolyte solutions respectively b) separating the two chambers with an ion-conducting membrane c) equipping the chambers with electrodes d) filling the inventive solution as redox active material in the catholyte chamber e) filling an anolyte solution comprising another redox active material in the anolyte chamber.

A further embodiment of the invention is a redox-flow cell obtained by the inventive process for making a redox-flow cell.

A further embodiment of the invention is the use of the inventive redox flow cell for storing electrical energy.

The inventive solution comprising water, 20 to 55 wt.-% according to the total weight amount of the solution of compound 2,2,6,6-tetramethyl-4-(trimethylammonio)-1-piperidinyloxy of formula (I), 0.1 to 6 wt.-% according to the total weight amount of the solution of an alkali metal cation, 0.5 to 12.5 wt.-% according to the total weight amount of the solution of compound N,N,N,1,2,2,6,6-octamethyl-4-piperidinammonium-1-oxide of formula (II) and 0.1 to 20 wt.-% according to the total weight amount of the solution of compound 2,2,6,6-hexamethyl (dimethylamino)-1-piperidinyloxy-N-oxide of formula (III).

The compound of formula (I) is preferably the main compound according to all compounds of formula (I), (II), (III) and the alkali metal cation in the inventive solution. Preferably, the amount of compound of formula (I) in the inventive solution is in the range of 20 to 55 wt.-%, particular in the range from 35 to 50 wt.-%, more preferably in the range of 40 to 45 wt.-% according to the total amount of the solution.

The inventive solution also comprises alkali metal cations. Preferably, these alkali metal cations are selected from the group of Na and K, more preferably is Na the alkali metal cation. The amount of the alkali metal cation in the inventive solution is preferably in the range of 0.1 to 6 wt.-%, particular in the range from 0.3 to 3.0 wt.-%, more preferably in the range of 0.5 to 1.7 wt.-% according to the total amount of the solution.

The compound of formula (II) is one resulting from the oxidation of one of the two byproducts formed by methylation of the starting compound of formula (IV) in the inventive process. Preferably, the amount of compound of formula (II) in the inventive solution is in the range from 0.5 to 12.5 wt.-%, particular in the range of 0.5 to 5.0 wt.-%, more preferably in the range of 2.0 to 3.0 wt.-% according to the total amount of the solution.

The compound of formula (III) is the other or second resulting from the oxidation of one of the two byproducts formed by methylation of the starting compound of formula (IV) in the inventive process. Preferably, the amount of compound of formula (III) in the inventive solution is in the range of 0.1 to 20 wt.-%, particularly in the range from 0.1 to 5.0 wt.-%, more preferably in the range of 0.1 to 1.5 wt.-% according to the total amount of the solution.

The sum of all amounts of compounds of formula (I), (II), (III) and the alkali metal cation is preferably in range from 20 to 50 wt.-%, particular in the range from 30 to 50 wt.-%, more preferably in the range from 40 to 50 wt.-% according to the total amount of the solution.

The amount of water in the inventive solution is preferably in the range from 35 to 75 wt.-% particularly in the range from 45 to 70 wt.-%, more preferably in the range from 50 to 60 wt.-% according to the total amount of the solution.

Preferably the pH-value of the inventive solution is in the range of 2 to 7, particularly in the range of 3 to 5, more preferably in the range of 4 to 5.

In the inventive solution, the anions present as counterions for the cationic species, are selected from the group of chloride, fluoride, perchlorate, sulfate, alkylsulfonate, arylsulfonate, phosphate, alkylphosphonate, arylphosphonate and nitrate or mixtures thereof. Preferably the anions are selected from the group of chloride, nitrate, sulfate and perchlorate, more preferably the anion is chloride. As the chloride anions are the most preferred ones, they should account for at least 90 mol % of the total anions, preferably at least 95 mol % of all the anions and more preferably more than 99 mol % of all the anions in the inventive solution.

The inventive solution is obtained by the inventive process. The inventive process comprising the following steps:

i) reacting the compound N,N,2,2,6,6-hexamethyl-4-piperidinamine of formula (IV)

(IV)

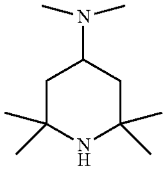

with water and methyl chloride to obtain an aqueous solution comprising compound N,N,N,2,2,6,6-heptamethyl-4-piperidinaminium of formula (V), compound N,N,N,1,2,2,6,6-octamethyl-4-piperidinaminium of formula (VI) and non-reacted compound N,N,2,2,6,6-hexamethyl-4-piperidinamine of formula (IV)

(IV)

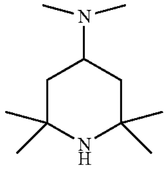

(V)

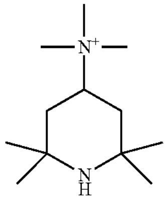

(VI)

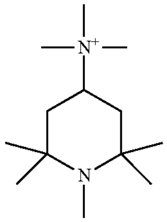

ii) reacting the resulting aqueous mixture of step i) with an aqueous hydrogen peroxide solution in the present of a catalyst selected from the group of alkali metal carbonate, alkali metal hydrogencarbonate, $CO_2$ and mixtures of those, iii) adding an acid to the resulting mixture of step ii) until the pH-value is in the range of 2 to 7, iv) partially removing water until the concentration of compound of formula (I) is in the range of 20 to 55 wt.-% according to the inventive solution.

For the first step of the inventive process the compound of formula (IV) is dissolved in water. Preferably, the mass ratio between the compound of formula (IV) in the feed mixture and water is in the range from 0.1 to 5, particularly in the range from 0.3 to 2, more preferably in the range from 0.7 to 1.2.

In the first step i) of the inventive process the starting compound of formula (IV) dissolved in water is methylated with methyl chloride. Preferably, the aqueous solution of compound of formula (IV) is methylated with 0.7 to 1.2 mol, particularly 0.9 to 1.2 mol, more preferably with 1.0 to 1.1 mol methyl chloride per mol of compound of formula (IV) in the feed mixture. The phrase "of compound of formula (IV) in the feed mixture" shall mean the amount of compound of formula (IV) that is dissolved in water in step i) at the beginning and not the amount of compound of formula (IV) that still remains in the solution after methylation in step i). During this methylation the temperature of the reaction is preferably in the range of 0 to 60° C., particularly in the range from 0 to 40° C., more preferably between 15 to 25° C. The temperature can be controlled by external heating, cooling or by slowly adding the methyl chloride to the aqueous solution of compound of formula (IV) so that the temperature will not rise above 60° C. Preferred is the slow addition of methyl chloride and the use of external cooling so that the temperature does not rise above 60° C.

The resulting mixture of step i) of the inventive process comprises water, the compounds of formula (V), (VI) and unreacted compound of formula (IV). This resulting aqueous mixture of step i) reacts with an aqueous hydrogen peroxide solution and an alkali metal catalyst selected from the group of alkali metal carbonate, alkali metal hydrogen carbonate, $CO_2$ and mixtures of those in step ii) of the inventive process. Preferably the catalyst is selected from the group of $Na_2CO_3$, $K_2CO_3$, $NaHCO_3$, $KHCO_3$, $CO_2$ and mixture of those, particularly the catalyst is selected from the group of $Na_2CO_3$ and $NaHCO_3$, more preferably $NaHCO_3$ is used as catalyst. The mixtures of the selected catalysts are selected from the group of $Na_2CO_3$ with $NaHCO_3$, $K_2CO_3$ with $KHCO_3$, $Na_2CO_3$ with $KHCO_3$, $K_2CO_3$ with $NaHCO_3$, $Na_2CO_3$ with $CO_2$, $K_2CO_3$ with $CO_2$, $NaHCO_3$ with $CO_2$ and $KHCO_3$ with $CO_2$. A preferred mixture is selected from the group of $NaHCO_3$ and $Na_2CO_3$.

The amount of catalyst used in step ii) of the inventive process is preferably in the range from 0.005 to 0.4 mol, particular in the range from 0.01 to 0.2 mol, more preferably in the range from 0.02 to 0.1 mol per mol of compound of formula (IV) in the feed mixture used in step i) of the inventive process.

Step ii) of the inventive process is an oxidation step wherein the compounds of formula (IV), (V) and (VI) are oxidized to the compounds of formula (I), (II) and (III). Therefore, the resulting aqueous mixture of step i) reacts preferably with 1.5 to 5 mol, particular with 1.5 to 3 mol, more preferably with 1.7 to 2.3 mol of an aqueous hydrogen peroxide solution per mol of the compound of formula (IV) in the feed mixture used in step i) of the inventive process and in the presence of the catalyst.

Preferably the concentration of the aqueous hydrogen peroxide solution used in step ii) of the inventive process is in the range from 25 to 70 wt.-%, particularly 30 to 70 wt.-%, more preferably 45 to 70 wt.-% of hydrogen peroxide.

During the oxidation the temperature of step ii) of the inventive process is preferably in the range from 20 to 80° C., particularly in the range from 40 to 60° C., more preferably in the range from 50 to 60° C. During the addition of the aqueous solution of hydrogen peroxide the pH-value of the reaction solution in step ii) of the inventive process is preferably in the range from 7 to 10, particularly in the range from 8 to 10, more preferably in the range from 8 to 9. The regulation of the pH-value during the oxidation in step ii) of the inventive step will be done by adding an acid or base. The acid for the regulation of the pH-value in step ii) of the inventive process is selected from the group of hydrogen chloride, perchloric acid, sulfuric acid, phosphoric acid, nitric acid, methanesulfonic acid, para-toluenesulfonic acid, methylphosphonic acid or phenylphosphonic acid. Preferred acids are hydrogen chloride, sulfuric acid, nitric acid and perchloric acid. More preferred is hydrogen chloride. Hydrogen chloride can be added as a gas or in form of an aqueous solution. Preferably an aqueous solution of hydrogen chloride, commonly known as hydrochloric acid is used. The base for regulation of the pH-value in step ii) of the inventive process is selected from the group of NaOH, and KOH, more preferred is NaOH. Normally the addition of the aqueous hydrogen peroxide solution leads to a decrease in the pH-value of the solution during oxidation in step ii) of the inventive process. Therefore, the initial pH value has to be adjusted by adding base. The use of a base, preferably NaOH, to keep the pH-value in the range of 7 to 10 during oxidation, is preferred.

After finishing the addition of the aqueous hydrogen peroxide solution the resulting mixture of step ii) of the inventive process will be stirred at the condition of step ii), which means around 60° C. and a pH-value in the range von 7 to 10, until the concentration of hydrogen peroxide in this solution is less than 0.5 wt.-%. The amount of hydrogen peroxide remaining is determined by cerimetric titration of the solution before and after catalytic decomposition of hydrogen peroxide with manganese dioxide. The difference between the two titration values is used to calculate the residual amount of hydrogen peroxide.

After the addition of the aqueous hydrogen peroxide solution is completed and the hydrogen peroxide concentration has decreased to less than 0.5 wt.-% in the solution obtained in step ii), the pH-value of this solution will be adjusted in step iii) of the inventive process by adding an acid. Preferably the pH-value after the addition of acid is in the range from 2 to 7, particular in the range from 3 to 5, more preferably in the range from 4 to 5. The acid used for decreasing the pH-value is selected from the group of hydrogen chloride, perchloric acid, sulfuric acid, phosphoric acid, nitric acid and methanesulfonic acid. Preferred acids are hydrogen chloride, sulfuric acid, nitric acid and perchloric acid. More preferred is hydrogen chloride used as gas or in an aqueous solution known as hydrochloric acid.

In the last step of the inventive process the amount of water is reduced in step iv) of the inventive process. This will be preferentially done by distillation. The amount of water that is distilled off depends on the desired final concentration of compound of formula (I) in the final solution. Water must be distilled off until the resulting solution shows a content of compound of formula (I) in the range of 20 to 55 wt.-%, preferably in the range from 25 to 50 wt.-%, particular in the range from 35 to 50 wt.-%, more preferably in the range from 40 to 45 wt.-% according to the total weight amount of the solution. Preferably the distillation will be done at a pressure in the range of 0.02 to 1.0 bar and a temperature in the range of 20 to 100° C., particular at a pressure in the range of 0.05 to 0.3 bar and a temperature in the range of 30 to 70° C., more preferably at a pressure in the range of 0.08 to 0.2 bar and a temperature in the range of 58 to 62° C.

After concentration, the inventive solution obtained can be used without further treatment as an electrolyte in a redox-flow cell. Preferably the inventive solution is used as catholyte in such a redox-flow cell. The redox-flow cell is normally built up by using two chambers for catholyte and anolyte solution each connected via a pump to a storage tank for catholyte and anolyte solution respectively. Both chambers are separated by an ion-conducting membrane and equipped with electrodes. In the cathode chamber and the connected storage tank of the cathode the inventive solution is filled. In the anode chamber and the connected storage tank of the anode the electrolyte for the anode is filled. The redox active compounds in the redox-flow cell change during charging and discharging between their different redox levels. For discharging the electrolyte has to be pumped from the storage tank to the electrode while for charging the inverse process is used. Therefore, the redox-flow cell comprising the inventive solution as electrolyte is an easy and multifunctional way to storage electrical energy for different applications.

EXAMPLES

General pH-Values:

pH values are always measured using a calibrated glass electrode (EasyFerm Plus PHI S8 225, two-point calibration with buffer pH=4.00 (citric acid, sodium hydroxide, sodium chloride from Fluka) and buffer pH=7.00 (potassium dihydrogen phosphate, disodium hydrogen phosphate from Fluka).

$^1$H-NMR Method:

$^1$H-NMR data of compound of formula (V):

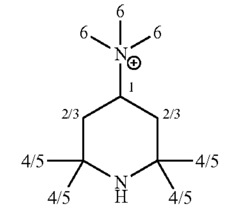

$^1$H-NMR (500 MHz, $D_2O$): δ [ppm]=3.68 (tt, J=12.5 Hz, 2.8 Hz 1H, $H_1$), 3.07 (s, 9H, $H_6$), 2.02-2.08 (m, 2H, $H_3$), 1.32 (t, J=12.5 Hz, 2H, $H_2$), 1.14 (s, 6H, $H_5$), 1.12 (s, 6H, $H_4$).

$^1$H-NMR Data of Compound of Formula (VI):

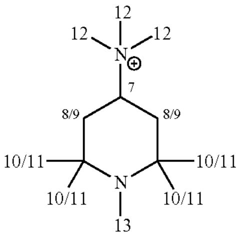

$^1$H-NMR (500 MHz, $D_2O$): 6 [ppm]=3.62 (tt, J=12.5 Hz, 3.1 Hz, 1H, $H_7$), 3.00 (s, 9H, $H_{12}$), 2.15 (s, 3H, $H_{13}$), 2.08-2.02 (m, 2H, $H_9$), 1.55 (t, J=12.5 Hz, 2H, $H_8$), 1.15 (s, 6H, $H_{11}$), 1.05 (s, 6H, $H_{10}$).

$^1$H-NMR Data of Compound of Formula (IV):

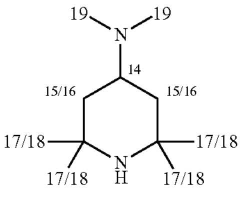

$^1$H-NMR (500 MHz, $D_2O$): δ [ppm]=2.83 (tt, J=12.3 Hz, 3.2 Hz, 1H, $H_{14}$), 2.27 (s, 6H, $H_{19}$), 1.88 (dd, J=12.7 Hz, 3.2 Hz, 2H, $H_{15}$), 1.28 (s, 6H, $H_{17}$), 1.24 (s, 6H, $H_{18}$), 1.17 (dd, J=12.7 Hz, 12.3 Hz, 6H, $H_{16}$).

The molar ratio of compound of formula (IV), (V) and (VI) can be determined most conveniently by comparing the integrals of the $^1$H-NMR signals at δ=3.68 ppm (1H from compound of formula (V)), 2.15 ppm (3H from compound of formula (VI)) and 2.27 ppm (6H from compound of formula (IV)).

Thus the molar ratio of compound of formula (IV):(V):(VI) is the same as the ratio of the following integrals: (integral of signal at δ=3.68 ppm from compound of formula (V)):(integral of signal at δ=2.15 ppm from compound of formula (VI))/3:(integral of signal at δ=2.27 ppm from compound of formula (IV))/6

$^1$H-NMR Measurements of the Inventive Solution:

Prior to $^1$H-NMR measurements, the inventive solution is reacted with excess phenyl hydrazine (approx. 2 mol per mol of compound of formula (I) plus compound of formula (III)) to convert the N-oxyl radicals to the corresponding hydroxylamines. This procedure yields two isomeric forms of each reduced species (compound of formula (Ia) and (Ib)/compound of formula (IIIa) and (IIIb)) and each isomer gives individual signals in the $^1$H-NMR spectrum. For all $^1$H-NMR measurements the crude reaction mixture from reduction with phenyl hydrazine was diluted with $D_2O$ and referenced to the signal of residual $H_2O$ protons at δ=4.79 ppm.

Signal assignments for compound of formula (I) were confirmed by synthesizing compound of formula (I) as a pure crystalline material as described in WO 2018/2883011 on page 28. Signal assignments for compound of formula (III) were confirmed by synthesizing compound of formula (III) as a pure material in aqueous solution as described here.

Synthesis of Compound of Formula (III) in Pure Form in Aqueous Solution:

To a solution of compound of formula (IV) (39.3 g) in water (40.1 g), 37 wt.-% hydrochloric acid (11.97 g) is added, whereby the pH value of the solution decreases to 9.0. Then, solid sodium bicarbonate (2.71 g) is added and the mixture is heated to 60° C. When this temperature is reached a 50 wt.-% aqueous solution of hydrogen peroxide (46.4 g) is continuously added over a period of 4 hours. During addition the pH value decreases and is kept above 8.0 by the addition of a 50 wt.-% aqueous solution of sodium hydroxide (6.4 g) in five approximately equal portions. After the addition of the hydrogen peroxide is completed, stirring is continued for 12 hours. Then, the mixture is allowed to cool down to room temperature and analyzed by $^1$H NMR spectroscopy and ESI MS mass spectrometry. The mixture contains >99 wt.-% of compound of formula (III) as organic material as determined by $^1$H NMR.

The identity of compound of formula (I) and (III) is also supported by HRMS (ESI in ACN:$H_2O$:HCOOH=80:20:0.1, instrument: Q Extractive™ hybrid-quadrupole-orbitrap mass spectrometer, ThermoFisher).

$^1$H-NMR of the Reduced Form of Compound of Formula (I):

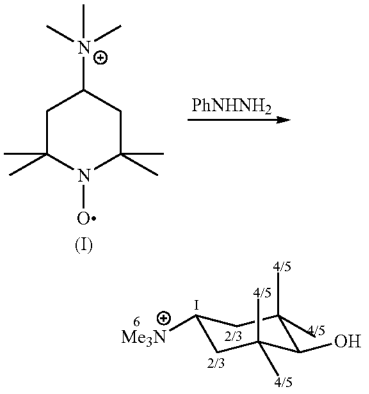

(I)

+

(Ia and Ib)

-continued

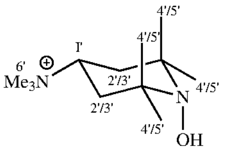

$^1$H-NMR (500 MHz, $D_2O$): δ [ppm]=3.80-3.67 (m, 1H, $H_1$+$H_{1'}$), 3.12 (s, 9H, $H_6$ or $H_{6'}$, minor isomer), 3.09 (s, 9H, $H_6$ or $H_{6'}$, major isomer), 2.24-2.14 (m, 2H, $H_2$+$H_{2'}$), 1.99 (t, J=12.1 Hz, 2H, $H_3$ or $H_{3'}$, minor isomer), 1.75 (t, J=12.4 Hz, 2H, $H_3$ or $H_{3'}$, major isomer), 1.34 (s, 6H, $H_{4/5}$ or $H_{4'/5'}$, minor isomer), 1.26 (s, 6H, $H_{4/5}$ or $H_{4'/5'}$, major isomer), 1.22 (s, 6H, $H_{4/5}$ or $H_{4'/5'}$, major isomer), 1.12 (s, 6H, $H_{4/5}$ or $H_{4'/5'}$, minor isomer). The ratio of the two isomers is approximately 90:10.

HRMS: theory for $C_{12}H_{26}N_2O^+$: 214.2040; found: 214.2036

$^1$H-NMR of the reduced form of compound of formula (III):

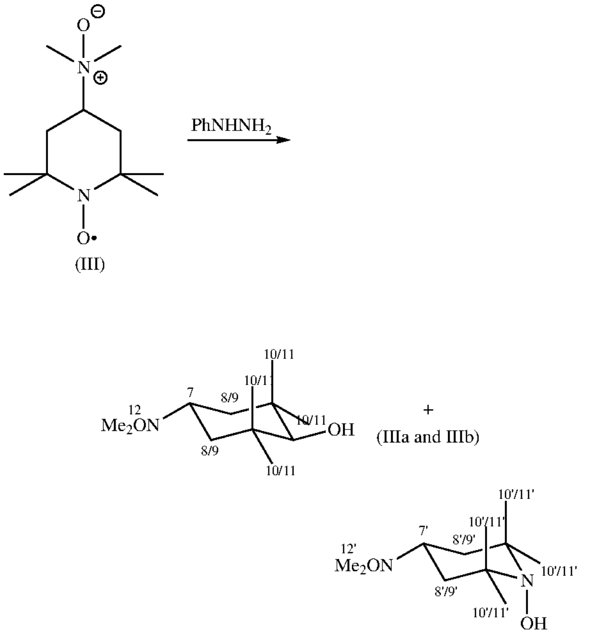

(III)

+ (IIIa and IIIb)

$^1$H-NMR (500 MHz, $D_2O$): δ [ppm]=3.66-3.52 (m, 1H, $H_7$+$H_{7'}$), 3.17 (s, 6H, $H_{12}$ or $H_{12'}$, minor isomer), 3.14 (s, 6H, $H_{12}$ or $H_{12'}$, major isomer), 2.27-2.14 (m, 2H, $H_8$+$H_{8'}$), 1.93 (t, J=12.5 Hz, 2H, $H_9$ or $H_{9'}$, minor isomer), 1.72 (t, J=12.5 Hz, 2H, $H_9$ or $H_{9'}$, major isomer), 1.33 (s, 6H, $H_{10/11}$ or $H_{10'/11'}$, minor isomer), 1.25 (s, 6H, $H_{10/11}$ or $H_{10'/11'}$, major isomer), 1.21 (s, 6H, $H_{10/11}$ or $H_{10'/11'}$, major isomer), 1.11 (s, 6H, $H_{10/11}$ or $H_{10'/11'}$, minor isomer). The ratio of the two isomers is approximately 86:14.

HRMS: theory for $C_{11}H_{24}N_2O_2^+$: 216.1638; found: 216.1637

Compound of formula (II) remains unchanged in the reduction and gives signals that are well separated from the signals from compounds of formula (Ia), (Ib), (IIIa) and (IIIb):

(II)

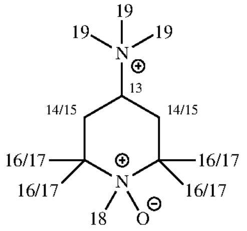

$^1$H-NMR (500 MHz, $D_2O$): δ [ppm]=3.93 (tt, J=13.3 Hz, 3.2 Hz, 1H, $H_{13}$), 3.14 (s, 9H, $H_{19}$), 3.03 (s, 3H, $H_{18}$), 2.47 (t, J=12.6 Hz, 2H, $H_{14}$), 2.07 (d, J=12.1 Hz, 2H, $H_{15}$, 1.65 (s, 6H, $H_{16}$), 1.56 (s, 6H, $H_{17}$).

HRMS: theory for $C_{13}H_{29}N_2O^+$: 229.2274; found: 229.2271

The ratio of compound of formula (I), (II) and (III) can be determined most conveniently by comparing the integrals of the $^1$H-NMR signals at δ=3.80-3.67 ppm (1H from compound of formula (I)), 1.56 ppm (6H from compound of formula (II)) and 3.66-3.52 ppm (1H from compound of formula (III)).

Thus the molar ratio of compound of formula (I):(II):(III) is the same as the ratio of the following integrals:

(integral of signal at δ=3.80-3.67 ppm from compound of formula (I)):(integral of signal at δ=1.56 ppm from compound of compound (II))/6: (integral of signal at δ=3.66-3.52 ppm from compound of formula (III)).

Cerimetric Redox Titration:

Cerimetric redox titration is used to determine the total content of hydrogen peroxide and N-oxyl species (compound of formula (I) and (III)) according to the following method:

Content of N-Oxyl Species:

100 mg of manganese dioxide is added to _pprox. 1 g of analyte. The mixture is stirred at 20 to 25° C. for 5 minutes or until 5 minutes after the end of gas evolution. Then the analyte is filtered. 250±2 mg of filtered analyte is placed in a beaker equipped with a magnetic stirring bar and is diluted with 45 mL purified water and 5 mL dilute sulfuric acid (10 wt.-% in water). The obtained solution is placed on an automated titration device (905 Titrando, Metrohm) equipped with a PtTitrode (Metrohm) and is stirred at 20-25° C. Cerium (IV) sulfate solution (0.10 mol/L) is added via the titration device until a redox potential jump is detected ($V_{C1}$). The concentration of the sum of compound of formula (I)+(III) in weight-%, $w_{I+III}$, can then be calculated from the consumption of cerium (IV) sulfate solution using the following equation:

$$W_{I+III} = 100 * \frac{V_{c1} * C_c}{m_s} * [(x_I * M_{I-Cl}) + (x_{III} * M_{III})]$$

Where the symbols have the following meaning:

$V_c$ is the volume of the cerium sulfate solution used given in liter $C_{c1}$ is the concentration of the cerium sulfate solution used given in mol/liter $m_s$ is the mass of the analyte given in grams $M_{I-Cl}$ is 249.8 g/mol, the molar mass of compound of formula (I) as the chloride salt $M_{III}$ is 215.3 g/mol, the molar mass of compound of formula (III)

$x_I$ is the molar fraction of compound of formula (I) calculated as the ratio of (integral at δ=3.80-3.67 ppm in $^1$H-NMR): [(integral of signal at δ=3.66-3.52 ppm in $^1$H-NMR)+(integral at δ=3.80-3.67 ppm in $^1$H-NMR)]

$x_{III}$ is the molar fraction of compound of formula (III) calculated as the ratio of (integral of signal at δ=3.66-3.52 ppm in $^1$H-NMR): [(integral of signal at δ=3.66-3.52 ppm in $^1$HNMR)+(integral at δ=3.80-3.67 ppm in $^1$H-NMR)]

Sum of Hydrogen Peroxide and N-Oxyl Species:

250±2 mg of analyte is placed in a beaker equipped with a magnetic stirring bar and is diluted with 45 mL purified water and 5 mL dilute sulfuric acid (10 wt.-% in water). The obtained solution is placed on an automated titration device (905 Titrando, Metrohm) equipped with a PtTitrode (Metrohm) and is stirred at 20-25° C. Cerium (IV) sulfate solution (0.10 mol/L) is added via the titration device until a redox potential jump ($V_{C2}$) is detected. The concentration of hydrogen peroxide can be calculated from the difference of the consumptions of cerium (IV) sulfate solution ($\Delta V_C = V_{C2} - V_{C1}$) using the following equation:

$$w_{H_2O_2} = 100 * \frac{\Delta V_c * C_c}{m_s} * M(\mathrm{H_2O_2})$$

Where the symbols have the same meanings as defined above and $M_{H2O2}$ is 34.0 g/mol, the molar mass of hydrogen peroxide.

Cyclic Voltammetry Method:

The solution obtained from the respective example is diluted with 0.1 mol/L aqueous sodium chloride solution until the concentration of the N-oxyl compounds is 1.0 wt.-%. Said solution is placed in an electrochemical cell equipped with a standard 3 electrode setup (working electrode: glassy carbon (ø=2 mm), counter electrode: platinum wire, reference electrode: Ag/AgCl, 3 mol/L KCl in water). The potential is ramped to 1200 mV and then cycled between 1200 mV and −700 mV at a scan rate of ±20 mV/s (in total 3 cycles) using PGU 20V-2A-E potentiostat (IPS).

Example 1

In a stainless-steel autoclave 800 ml of water and 645 g of N,N,2,2,6,6-hexamethylpiperidin-4-amine compound of formula (IV) are mixed and tempered to 20° C. Then 185.5 g of methyl chloride are pressed within 70 minutes into the autoclave at approx. 3.2 bar. The mixture is consequently stirred at 20 to 25° C. for 6 hours. The autoclave is depressurized afterwards and purged with nitrogen for approx. 10 minutes. 1630 g of an aqueous solution of compound of formula (IV), (V) and (VI) is obtained (50 wt.-% organics in water). The molar ratio of compound of formula (IV):(V):(VI) as determined by $^1$H-NMR is 2.5:92.8:4.7, which corresponds to 1.0 wt.-% of compound of formula (IV), 46.5 wt.-% of compound of formula (V) chloride salt and 2.5 wt.-% of compound of formula (VI) chloride salt.

Example 2 (Comparative)

The methylation was made as described in the WO 2018/28830, page 27, line 20 to page 28 line 15 (equal to DE102016009904A1, paragraph [0112] and following). In the $^1$H-NMR of the product obtained, only signals for compound of formula (V) are visible.

Example 3

To a solution taken from example 1 (100 g, contains 1.0 wt.-% of compound of formula (IV), 46.5 wt.-% of compound of formula (V) chloride salt and 2.5 wt.-% of compound of formula (VI) chloride salt in water) 37 wt.-% hydrochloric acid (1.67 g) is added, whereby the pH value of the solution decreases to 9.0. Then, solid sodium bicarbonate (2.79 g) is added and the mixture is heated to 60° C. When the temperature is reached a 50 wt.-% aqueous solution of hydrogen peroxide (32.7 g) is continuously added over a period of 4 hours. During addition the pH value decreases and is kept above 8.0 by adding a 50 wt.-% aqueous solution of sodium hydroxide (1.73 g) in five approximately equal portions. After the addition of the hydrogen peroxide is completed, stirring is continued for 12 hours. The mixture is then allowed to cool down to about 30° C. and 37 wt.-% hydrochloric acid (ca. 2 g) is added to decrease the pH value of the solution to 4.5. Water is subsequently distilled off at reduced pressure (70 mbar abs) until the concentration of the N-oxyl species of compound of formula (I) and (III) is 46 wt.-% (as determined by cerimetric redox titration).

The molar ratio of compound of formula (I):(II):(III) as determined by $^1$H-NMR is 93.0:4.7:2.3, which corresponds to 45.0 wt.-% of compound of formula (I) chloride salt, 2.4 wt.-% of compound of formula (II) chloride salt and 1.0 wt.-% of compound of formula (III).

Example 4

To a solution taken from example 1 (100 g, contains 1.0 wt.-% of compound of formula (IV), 46.5 wt.-% of compound of formula (V) chloride salt and 2.5 wt.-% of compound of formula (VI) chloride salt in water) 37 wt.-% hydrochloric acid (5.83 g) is added, whereby the pH value of the solution decreases to 8.5. Then, solid sodium carbonate (1.17 g) is added and the mixture is heated to 40° C. When the temperature is reached, a 50 wt.-% aqueous solution of hydrogen peroxide (32.7 g) is continuously added over a period of 6 hours. During addition the pH value decreases and is kept above 8.0 by adding a 50 wt.-% aqueous solution of sodium hydroxide (6.39 g) in five approximately equal portions. After the addition of the hydrogen peroxide is completed, stirring is continued for 12 hours. The mixture is then allowed to cool down to about 30° C. and 37 wt.-% hydrochloric acid (ca. 2.5 g) is added to adjust the pH value of the solution to 4.0. Water is subsequently distilled off at reduced pressure (70 mbar abs) until the concentration of N-oxyl species of compound of formula (I) and (III) is 48 wt.-% (as determined by cerimetric redox titration).

The molar ratio of compound of formula (I):(II):(III) as determined by $^1$H-NMR is 93.1:4.8:2.1 which corresponds to 47.1 wt.-% of compound of formula (I) chloride salt, 2.6 wt.-% of compound of formula (II) chloride salt and 0.9 wt.-% of compound of formula (III).

Example 5 (Comparative)

The oxidation was performed as described in the WO 2018/028830, page 28, line 20 to page 29 line 22. In HRMS of the product obtained no signals for compound of formula (II) and (IIIa)/(IIIb) are visible; in $^1$H-NMR of the reduced samples only signals for compound of formula (Ia/Ib) are visible.

Example 6

Cyclic voltammetry of product of example 3 is measured (see FIG. I).

Example 7 (Comparative)

Cyclic voltammetry of example 5 is measured (see FIG. II).

The cyclic voltammogram in FIG. I is nearly identical to that of the comparative example 5 in FIG. II. Therefore, the inventive solution of example 3 shows nearly the same redox potential as the solution obtained in example 5 which represents the state of the art. The inventive solution can thus be used in a redox flow cell as it is described in the state of the art.

The invention claimed is:

1. A solution comprising:

a) water, b) 20 to 55 wt. 2,2,6,6-tetramethyl-4-(trimethylammonio)-1-piperidinyloxy of formula (I), (I)

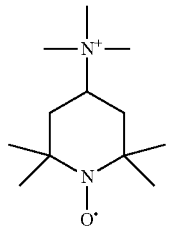

c) 0.1 to 6 wt.-% alkali metal cations, d) 0.5 to 12.5 wt.-% N,N,N,1,2,2,6,6-octamethyl-4-piperidinammonium-1-oxide of formula (II), (II)

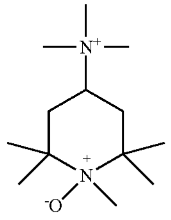

e) 0.1 to 20 wt.-% 2,2,6,6-hexamethyl-4-(dimethylamino)-1-piperidinyloxy-N-oxide of formula (III).

(III)

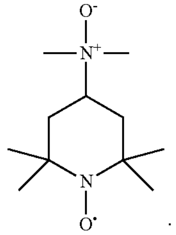

2. The solution according to claim 1, wherein the alkali metal cations are Na.

3. The solution according to claim 1, wherein the solution has a pH-value in the range of 2 to 7.

4. The solution according to claim 1, wherein the sum of the amounts of the compounds of formula (I), formula (II), formula (III), and the amount of alkali metal cations in the solution is in the range of 20 to 50 wt.-% according to the total weight amount of the solution.

5. A process for making a redox-flow cell comprising the following steps:

a) providing two chambers, a catholyte chamber and an anolyte chamber, each connected to at least one storage tank for catholyte and anolyte solutions respectively, b) separating the two chambers with an ion-conducting membrane, c) equipping the two chambers with electrodes, d) filling the solution according to claim 1 in the catholyte chamber, e) filling an anolyte solution comprising another redox active material in the anolyte chamber.

6. A process for the production of the solution according to claim 1, comprising the following steps:

i) reacting the compound N,N,2,2,6,6-hexamethyl-4-piperidinamine of formula (IV) with water and methyl chloride to get an aqueous mixture comprising compound N,N,N,2,2,6,6-heptamethyl-4-piperidiniaminium of formula (V), compound N,NN,1,2,2,6,6-octamethyl-4-piperidinaminium of formula (VI) and non-reacted compound N,N,2,2,6,6-hexamethyl-4-piperidinamine of formula (IV), ii) reacting the resulting aqueous mixture of step i) with an aqueous hydrogen peroxide solution the presence of a catalyst selected from the group of alkali metal carbonate, alkali metal hydrogencarbonate, $CO_2$ and mixtures thereof, iii) adding an acid to the resulting mixture of step ii) until the pH-value decreases in the range of 2 to 7, iv) partially removing water until the concentration of compound of formula (I) is in the range of 20 to 55 wt.-% according to the solution of claim 1.

7. The process of claim 6 wherein in step i) of the process the compound of formula (IV) is reacted with methyl chloride and water at a temperature in the range of 0 to 60° C.

8. The process according to claim 6 wherein in step i) of the process the compound of formula (IV) is reacted with 0.7 to 1.2 mol methyl chloride in the presence of water and the mass ratio between compound of formula (IV) in the feed mixture and water is in the range of 0.1 to 5.

9. The process according of claim 6 wherein in step ii) of the process the resulting mixture of step i) is reacted with an aqueous hydrogen peroxide solution in the presence of the catalyst at a temperature in the range of 20 to 80° C. wherein the pH-value during the addition of the aqueous hydrogen peroxide solution is maintained between 7 and 10.

10. The process according to claim 6 wherein in step ii) of the process 1.5 to 5 mol of aqueous hydrogen peroxide having a concentration in the range of 25 to 70 wt.-% per mol of compound of formula (IV) in the feed mixture is reacted in the presence of 0.005 to 0.4 mol of the catalyst per mol of compound of formula (IV) in the feed mixture.

11. The process according to claim 6 wherein the addition of the acid in step iii) will start when the concentration of hydrogen peroxide in the mixture of step ii) has decreased to less than 0.5 wt.-%.

12. The process according to claim 6 wherein the acid in step iii) is hydrogen chloride acid.

* * * * *